(12) United States Patent
Ueda et al.

(10) Patent No.: US 9,901,727 B2
(45) Date of Patent: Feb. 27, 2018

(54) CONNECTOR

(71) Applicant: Terumo Kabushiki Kaisha, Tokyo (JP)

(72) Inventors: Yasuhiro Ueda, Yamanashi (JP); Yasunobu Zushi, Yamanashi (JP); Kouhei Taoka, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 346 days.

(21) Appl. No.: 14/340,311

(22) Filed: Jul. 24, 2014

(65) Prior Publication Data

US 2014/0332091 A1 Nov. 13, 2014

Related U.S. Application Data

(63) Continuation of application No. PCT/JP2013/052133, filed on Jan. 31, 2013.

(30) Foreign Application Priority Data

Jan. 31, 2012 (JP) .................................. 2012-018326

(51) Int. Cl.
*A61M 39/10* (2006.01)
*A61M 39/26* (2006.01)
*A61M 39/04* (2006.01)

(52) U.S. Cl.
CPC ............ *A61M 39/10* (2013.01); *A61M 39/26* (2013.01); *A61M 39/045* (2013.01);
(Continued)

(58) Field of Classification Search
CPC .. A61M 2039/1072; A61M 2039/1083; A61M 2039/1088; A61M 2205/0216;
(Continued)

(56) References Cited

U.S. PATENT DOCUMENTS 4,819,684 A 4/1989 Zaugg et al.
5,203,775 A 4/1993 Frank et al.
(Continued)

FOREIGN PATENT DOCUMENTS

CN 1809398 A 7/2006
EP 1 792 639 A1 6/2007
(Continued)

OTHER PUBLICATIONS

Extended European Search Report dated May 27, 2015 issued in Application No. 13743848.7.
(Continued)

*Primary Examiner* — Theodore Stigell
*Assistant Examiner* — Benjamin Koo
(74) *Attorney, Agent, or Firm* — Foley & Lardner LLP

(57) ABSTRACT

A connector includes a housing having a flow path through which liquid passes, and a male connector connecting portion having a substantially circular tube hole communicating with the flow path; and a valve formed of an elastic material and adapted to block the male connector connecting portion of the housing. The valve includes a top surface exposed from the male connector connecting portion, a bottom surface opposite to the top surface, and a slit opened at least on the top surface or the bottom surface. The housing includes a stopping portion configured to be engaged with a tip end of a male connector to define an insertion length of the male connector.

19 Claims, 6 Drawing Sheets

(52) U.S. Cl.
CPC ... *A61M 39/105* (2013.01); *A61M 2039/1072* (2013.01); *A61M 2039/1083* (2013.01); *A61M 2039/1088* (2013.01); *A61M 2205/0216* (2013.01); *Y10T 137/0491* (2015.04); *Y10T 137/9029* (2015.04)

(58) Field of Classification Search
CPC .... A61M 39/105; A61M 39/26; A61M 39/10; A61M 39/045
See application file for complete search history.

(56) References Cited

U.S. PATENT DOCUMENTS

| | | | | |
|---|---|---|---|---|
| 5,251,873 | A | * | 10/1993 | Atkinson ............ A61M 39/045 251/149.1 |
| 6,171,287 | B1 | * | 1/2001 | Lynn ..................... A61M 39/02 251/149 |
| 6,468,251 | B1 | | 10/2002 | Yamanaka et al. |
| 2002/0038108 | A1 | | 3/2002 | Fujii |
| 2003/0066980 | A1 | * | 4/2003 | Hishikawa ............ A61M 39/26 251/149.1 |
| 2006/0184140 | A1 | | 8/2006 | Okiyama |
| 2008/0027375 | A1 | | 1/2008 | Kitani et al. |
| 2008/0086097 | A1 | | 4/2008 | Rasmussen et al. |
| 2010/0030195 | A1 | * | 2/2010 | Hishikawa ......... A61M 39/1011 604/535 |

FOREIGN PATENT DOCUMENTS

| | | |
|---|---|---|
| EP | 1 884 260 A1 | 2/2008 |
| EP | 2 042 214 A1 | 4/2009 |
| JP | 03-062113 B2 | 9/1991 |
| JP | 2002-095758 A | 4/2002 |
| JP | 3389983 B2 | 3/2003 |
| JP | 2008-029495 A | 2/2008 |
| JP | 2010-505551 A | 2/2010 |
| WO | WO 2008/043069 A2 | 4/2008 |

OTHER PUBLICATIONS

International Search Report dated May 7, 2013 issued in Application No. PCT/JP2013/052133.
Notification of Reasons for Refusal issued in Japanese Patent Application No. 2013-556487 dated Oct. 18, 2016.

* cited by examiner

CONNECTOR

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2013/052133 filed on Jan. 31, 2013, which is based upon and claims the benefit of priority of Japanese Application No. 2012-018326 filed on Jan. 31, 2012, the entire contents of which are hereby incorporated by reference in their entireties.

BACKGROUND

The present disclosure relates to a connector capable of connecting a male connector of various medical instruments, infusion containers or the like in a liquid-tight manner.

Conventionally, when performing fluid infusion, blood transfusion, hemodialysis or the like, liquid is infused into the body using a medical tube. Further, in the case where another liquid such as a medical solution or the like is to be merged into the liquid within the tube, a connector capable of connecting a male connector of a syringe, a lure taper member or the like and a medical tube to each other in a liquid-tight manner is used.

A male connector of a syringe, a lure taper member or the like may be referred to as a male lure, and a connector to be connected to the male lure may be referred to as a female lure.

An example of such connector capable of connecting a male connector is disclosed in Japanese Patent Publication No. 3389983 ("JP '983"). The connector disclosed in this document includes a disk-like valve which has an insertion hole formed on the central part thereof, a base which supports the lower part of the peripheral edge of the valve except the central part of a back surface of the valve, and a cover which fixedly supports the valve by covering at least the upper part of the peripheral edge of the valve except the central part of a front surface of the valve.

In the connector disclosed in JP '983, a male connector is retained in a mixed injection port by the edge end of the cover which forms a fitting hole with the male connector penetrating the valve. In this manner, holding/fixing of the male connector in the mixed injection port and communication between flow paths of the male connector and the mixed injection port are performed.

SUMMARY OF INVENTION

However, in the connector disclosed in JP '983, when a user pushes a male connector into the fitting hole, a slit of the valve may be torn. In particular, when inserting a tapered male connector whose diameter decreases toward the end thereof, a larger load is applied to the slit as the male connector is pushed deeper into the fitting hole. As a result, the slit is highly likely to be torn.

Further, in the connector disclosed in JP '983, the tip end of the male connector enters the flow path. Therefore, the tip end of the male connector comes into contact with liquid inside the flow path. Thus, if the tip end of the male connector has bacteria adhering thereon, the liquid inside the flow path will be disadvantageously contaminated.

In view of the above problems, it is one object of embodiments of the present invention to provide a connector that is capable of reliably allowing flow paths of a male connector and a housing to communicate with each other without causing the tip end of the male connector to penetrate a valve, and suppressing or preventing a slit of the valve from being torn.

A connector according to one embodiment of the present invention includes: a housing having a flow path through which liquid passes, and a male connector connecting portion having a substantially circular tube hole communicating with the flow path; and a valve formed of an elastic material and adapted to block the male connector connecting portion of the housing. The valve is formed in a substantially columnar shape, and includes: a top surface exposed from the male connector connecting portion; a bottom surface opposite to the top surface; and a slit opened at least on the top surface or the bottom surface. The housing includes a stopping portion which is adapted to be engaged with a tip end of the male connector to define an insertion length of the male connector.

In the connector having the above configuration, when a male connector is connected to the male connector connecting portion of the housing, the top surface of the valve is pressed by the male connector. The valve thereby elastically deforms to form an opening communicating with the flow path. As a result, the male connector communicates with the flow path of the housing though the opening formed by the valve.

Further, since the stopping portion of the housing defines the insertion length of the male connector, it is possible to prevent the male connector from penetrating the valve. Therefore, it is possible to reliably prevent the male connector from entering the flow path. Further, since the valve is not caused to deform more than necessary, it is possible to suppress or prevent the slit of the valve from being torn, and thereby maintain the air-tightness of the valve.

With the connector having the above configuration, since the stopping portion defines the insertion length of the male connector, the valve can be sufficiently opened without causing the tip end of the male connector to penetrate the valve. Therefore, it is possible to reliably prevent the male connector from entering the flow path, and prevent the slit of the valve from being torn.

DETAILED DESCRIPTION

Figure 1:
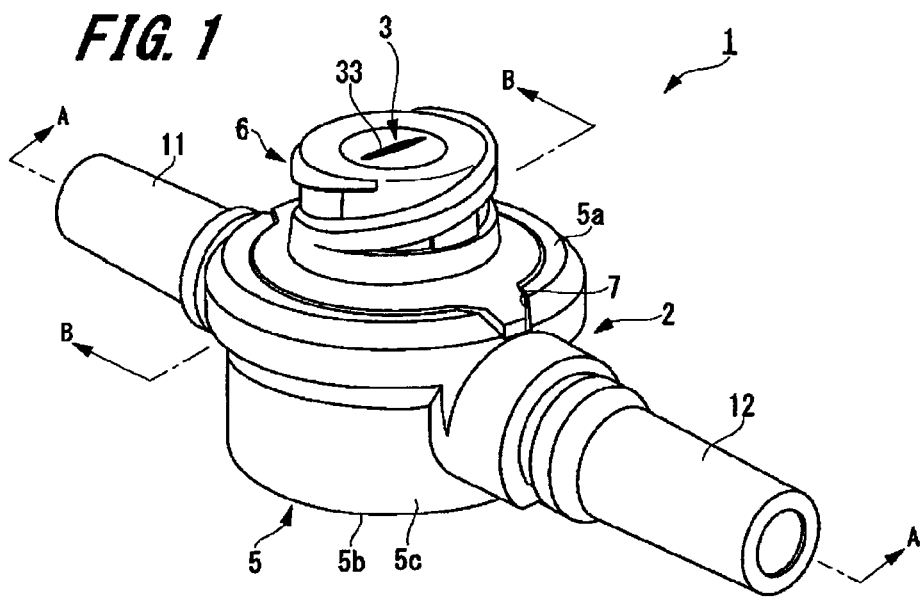
FIG. 1 is a perspective view illustrating a connector according to a first embodiment of the present invention.

Hereinbelow, embodiments of a connector according to the present invention will be described with reference to FIGS. 1 to 9. Note that, in the drawings, the same components are denoted by the same reference numerals. Further, the connector of the present invention is not limited to the embodiments described below.

1. First Embodiment of Connector

[Configuration Example of Connector]

First, the configuration of a connector according to a first embodiment of the present invention will be described with reference to FIGS. 1 to 4.

Figure 2:
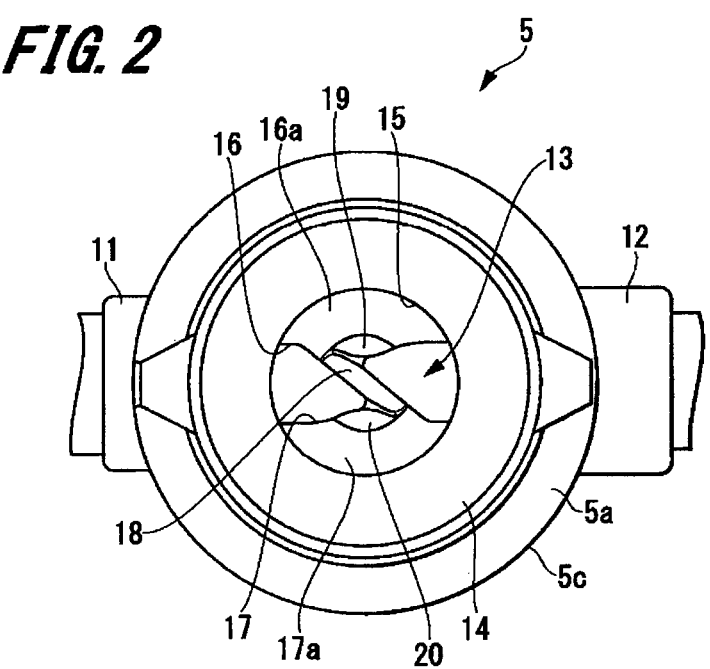
FIG. 2 is a plan view of a housing main body of the connector according to the first embodiment of the present invention.
Figure 3:
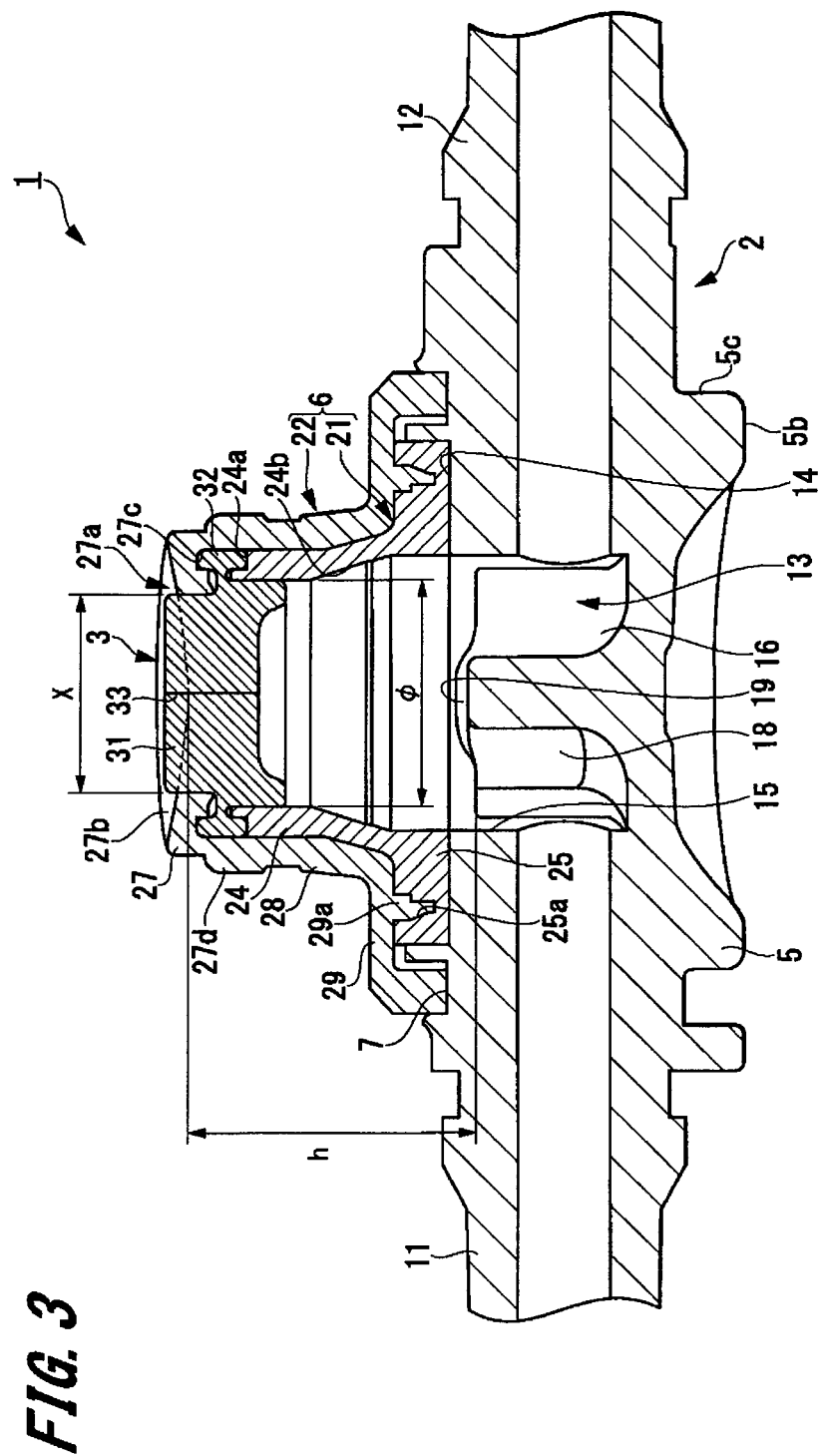
FIG. 3 is a cross-sectional view taken along line A-A of FIG. 1.
Figure 4:
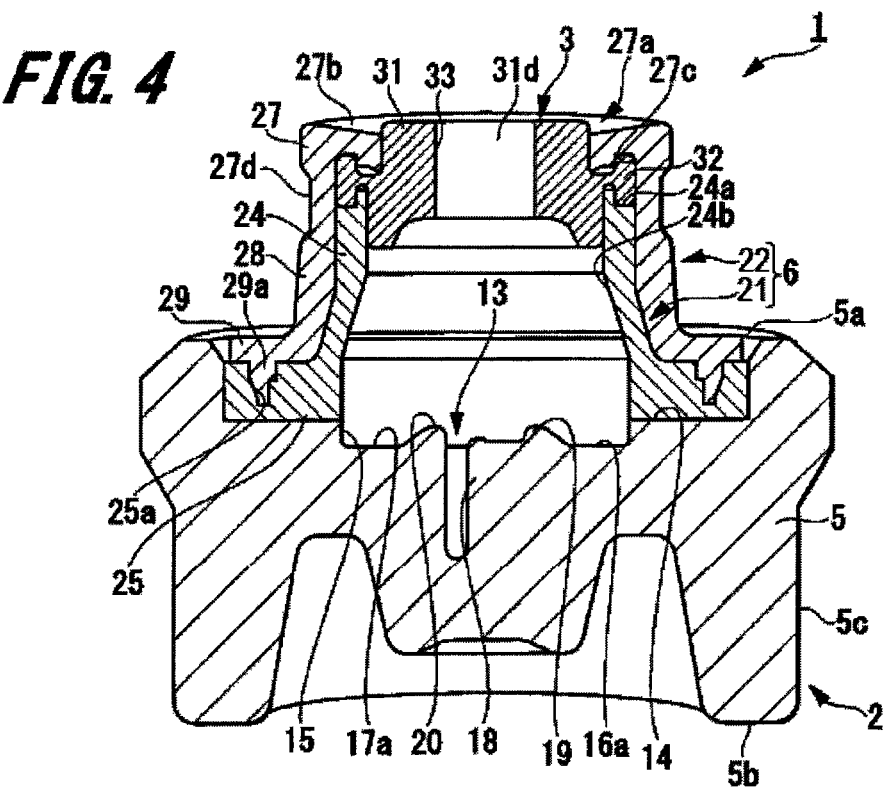
FIG. 4 is a cross-sectional view taken along line B-B of FIG. 1.

FIG. 1 is a cross-sectional view illustrating the connector according to the first embodiment. FIG. 2 is a plan view of a housing main body of the connector according to the first embodiment. FIG. 3 is a cross-sectional view taken along line A-A of FIG. 1. FIG. 4 is a cross-sectional view taken along line B-B of FIG. 1.

As illustrated in FIG. 1, a connector 1 includes a housing 2, and a valve 3 fixed to the housing 2.

[Housing]

Examples of the material of the housing 2 include polyolefins such as polyethylene, polypropylene, ethylene-propylene copolymers, and ethylene-vinyl acetate copolymers (EVA) and the like, polyvinyl chloride, polyvinylidene chloride, polystyrene, polyamide, polyimide, polyamide-imide, polycarbonate, poly(4-methylpentene-1), ionomers, acrylic resins, polymethyl methacrylate, acrylonitrile-butadienestyrene copolymer (ABS resin), acrylic-styrene copolymers (AS resins), butadiene styrene copolymers, polyesters such as polyethylene terephthalate (PET), polybutylene terephthalate (PBT), polycyclohexane terephthalate (PCT), polyether, polyether ketone (PEK), polyether ether ketone (PEEK), polyether imide, polyacetal (POM), polyphenylene oxide, denatured polyphenylene oxide, polysulfone, polyether sulfone, polyallylate, polyphenylene sulfide, polyarylate, aromatic polyester (liquid crystal polymers), polytetrafluoroethylene, polyvinylidene fluoride, and other fluororesins, a blended material or a polymer alloy each having at least one of the aforesaid materials as a component thereof. Examples of the material of the housing 2 also include various kinds of glass materials, ceramic materials, and metallic materials.

The housing 2 includes a housing main body 5, and a male connector connecting portion 6 joined to the housing main body 5. The housing main body 5 is a substantially columnar hollow casing, and has an upper surface 5a, a lower surface 5b, and an outer peripheral surface 5c, wherein the upper surface 5a is one end in the axial direction, and the lower surface 5b is the other end.

A first tube connecting port 11 and a second tube connecting port 12 are arranged on the outer peripheral surface 5c of the housing main body 5. The tube connecting ports 11, 12 are each formed in a cylindrical shape protruding from the outer peripheral surface 5c of the housing main body 5. Both of the axis of the first tube connecting port 11 and the axis of the second tube connecting port 12 coincide with the radial direction of the housing main body 5.

As illustrated in FIG. 2, a step portion 14 having a substantially circular shape is formed on the upper surface 5a of the housing main body 5. The male connector connecting portion 6 is fitted to the step portion 14. A flow path recess 15 is formed on the center of the step portion 14. The flow path recess 15 has a substantially circular planar shape, and communicates with the first tube connecting port 11 and the second tube connecting port 12. In other words, the flow path recess 15 forms a flow path 13 inside the housing main body 5.

Protruding walls 16, 17 are formed on an inner wall surface of the flow path recess 15. The protruding walls 16, 17 face each other in a direction perpendicular to the direction in which the first tube connecting port 11 and the second tube connecting port 12 face each other. Further, a connecting wall 18 is provided between the protruding wall 16 and the protruding wall 17. The connecting wall 18 is integrally formed with the protruding wall 16 and the protruding wall 17. Therefore, liquid such as a medical solution flowing from the first tube connecting port 11 flows over the connecting wall 18, and flows into the second tube connecting port 12. On the other hand, liquid such as a medical solution flowing from the second tube connecting port 12 flows over the connecting wall 18, and flows into the first tube connecting port 11.

An upper surface 16a of the protruding wall 16 and an upper surface 17a of the protruding wall 17 are located on the same plane. A stopping portion 19 is formed on the upper surface 16a of the protruding wall 16. A stopping portion 20 is formed on the upper surface 17a of the protruding wall 17. These stopping portions 19, 20 define an insertion length of a male connector 100 (described below, see FIG. 8). The stopping portions 19, 20 face each other in the direction perpendicular to the direction in which the first tube connecting port 11 and the second tube connecting port 12 face each other as with the protruding walls 16, 17.

The stopping portions 19, 20 are each formed in a projection shape protruding in an upper direction. The upper direction is opposite to an insertion direction of the male connector 100 with respect to the connector 1. Further, the stopping portions 19, 20 are each formed in a tapered shape whose diameter decreases toward the end thereof (see FIG. 4).

As illustrated in FIGS. 3 and 4, the male connector connecting portion 6 communicates with the flow path 13 of the housing 2. The male connector connecting portion 6 includes a first member 21 which is joined to the housing main body 5 and a second member 22 which is joined to the first member 21.

The first member 21 forms a base end of the male connector connecting portion 6. The first member 21 includes an inner tubular portion 24 and a flange portion 25. The inner tubular portion 24 is fitted into an outer tubular portion 28 (described below) of the second member 22.

A tube hole of the inner tubular portion 24 is formed in a circular shape. A fitting recess 24a for fitting thereinto a fixing portion 32 (described below) of the valve 3 is formed on one end in the axial direction of the inner tubular portion 24. Further, a tapered surface 24b is formed on an inner surface of the inner tubular portion 24, the inner surface forming the circular tube hole. The tapered surface 24b allows the diameter of the tube hole to increase toward the other end in the axial direction of the inner tubular portion 24.

The flange portion 25 is continuous with the other end in the axial direction of the inner tubular portion 24, and is formed in a ring-like shape protruding outward in the radial direction of the inner tubular portion 24. The outer diameter of the flange portion 25 is substantially equal to the diameter of the step portion 14 of the housing main body 5. The flange portion 25 is fitted to the step portion 14 so as to be joined to the housing main body 5. The flange portion 25 may also be joined to the housing main body 5 by other fixing methods such as adhesive, fusion, a fixing screw, and the like. An engagement groove 25a with which an engagement projection 29a (described below) of the second member 22 is engaged is formed on an upper surface of the flange portion 25.

The second member 22 forms a tip end of the male connector connecting portion 6. The second member 22 includes a connector fitting portion 27 into which the male connector 100 (see FIG. 8) is fitted, the outer tubular portion 28 which is continuous with the connector fitting portion 27, and an engagement portion 29 which is continuous with the outer tubular portion 28.

The connector fitting portion 27 is formed in a substantially cylindrical shape, and has a tube hole 27a. A tapered surface 27b is formed on an inner surface of the connector fitting portion 27. The tapered surface 27b allows the diameter of the tube hole 27a to increase toward one end in the axial direction of the connector fitting portion 27. By forming the tapered surface 27b, it is possible to easily insert the male connector 100 into the connector fitting portion 27.

A recess 27c for fitting thereinto the fixing portion 32 of the valve 3 is formed on the other end in the axial direction of the connector fitting portion 27. In other words, the male connector connecting portion 6 fixes the valve 3 by sandwiching the fixing portion 32 of the valve 3 between the inner tubular portion 24 of the first member 21 and the connector fitting portion 27 of the second member 22.

The outer tubular portion 28 is continuous with the other end in the axial direction of the connector fitting portion 27, and is formed in a cylindrical shape whose inner diameter is greater than the inner diameter of the connector fitting portion 27. The inner diameter of the outer tubular portion 28 is substantially equal to the outer diameter of the inner tubular portion 24 of the first member 21. The outer tubular portion 28 is fitted to an outer peripheral surface of the inner tubular portion 24 of the first member 21. The outer tubular portion 28 may also be fixed to the inner tubular portion 24 of the first member 21 by other fixing methods such as adhesive, fusion, a fixing screw, and the like.

The outer diameter of the outer tubular portion 28 is substantially equal to the outer diameter of the connector fitting portion 27. Further, a screw portion 27d is formed on outer peripheral surfaces of the connector fitting portion 27 and the outer tubular portion 28. The screw portion 27d is adapted to be screwed with a lock portion (so-called "lure lock", which is not illustrated) formed around the male connector with a predetermined distance therebetween.

The engagement portion 29 is continuous with the tip end in the axial direction of the outer tubular portion 28, and protrudes outward in the radial direction of the outer tubular portion 28. The engagement projection 29a is formed on a lower surface of the engagement portion 29. The engagement projection 29a is engaged with the engagement groove 25a formed in the first member 21. Further, the engagement portion 29 is fitted into a fitting recess 7 of the housing main body 5 so as to be joined to the housing main body 5.

The engagement portion 29 may also be fixed to the first member 21 and the housing main body 5 by other fixing methods such as adhesive, fusion, a fixing screw, and the like.

Next, the dimensions of the housing 2 will be described with reference to FIG. 3.

The diameter X of the tube hole 27a of the connector fitting portion 27 is determined according to the size of an upper portion 31A of a deformable portion 31 (described below, see FIG. 5) of the valve 3. The diameter X of the tube hole 27a will be described in more detail below when discussing the dimensions of the valve 3. Further, it is preferred that the distance h between the lower peripheral edge of the tapered surface 27b and the upper surfaces 16a, 17a of the protruding walls 16, 17 be within the range of 5 to 15 mm.

The diameter ϕ of the tube hole of the inner tubular portion 24 is determined according to the size of a lower portion 31B of the deformable portion 31 (described below, see FIG. 5) of the valve 3, and is preferably equal to or larger than 4 mm. The tube hole of the inner tubular portion 24 is a space necessary for the valve 3 to elastically deform (described below).

The diameter ϕ of the inner tubular portion 24 may be at least partially equal to or larger than 4 mm. For example, in the case where the diameter of tube hole of the inner tubular portion 24 continuously decreases toward the flow path 13, the diameter of the tube hole of the inner tubular portion 24 on the side of the connector fitting portion 27 may be equal to or larger than 4 mm.

[Valve]

Next, the valve 3 will be described with reference to FIGS. 5 to 7.

Figure 5:
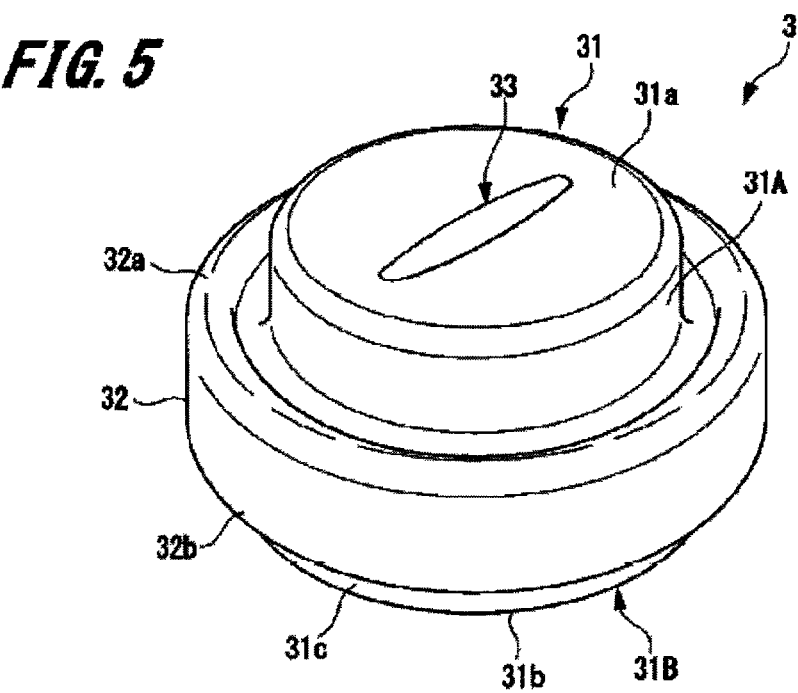
FIG. 5 is a perspective view of a valve of the connector according to the first embodiment of the present invention.

FIG. 5 is a perspective view of the valve 3. FIG. 6 is a plan view of the valve. FIG. 7 is a cross-sectional view taken along line C-C of FIG. 6.

The valve 3 is molded using a metal mold (not illustrated), and formed to be elastically deformable. Examples of the material of the valve 3 include various kinds of rubber such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluorocarbon rubber, various kinds of thermoplastic elastomers such as a styrene-based elastomer, a polyolefine-based elastomer, a polyvinyl chloride-based elastomer, a polyurethane-based elastomer, a polyester-based elastomer, a polyamide-based elastomer, a polybutadine-based elastomer, and a fluorocarbon rubber-based elastomer. Examples of the material of the valve 3 also include a blended material having one, two or more of the aforesaid materials as the component thereof.

Further, the hardness of the valve 3 is preferably within the range of 20° to 60° (hardness A). Accordingly, since moderate elastic force of the valve 3 can be ensured, it is possible to allow the valve 3 to elastically deform (described below).

As illustrated in FIG. 5, the valve 3 includes the deformable portion 31 where a slit 33 is formed, and the fixing portion 32 which is continuous with the deformable portion 31.

The deformable portion 31 is formed in a shape in which two columns having the same axis but different diameters are continuous with each other in the axial direction. Specifically, the deformable portion 31 has the upper portion 31A as an upper column and the lower portion 31B which is a column whose diameter is larger than the diameter of the upper portion 31A. The upper portion 31A forms a top surface 31a of the deformable portion 31. Further, the lower portion 31B forms a bottom surface 31b of the deformable portion 31. The fixing portion 32 is continuous with an outer peripheral surface 31c of the lower portion 31B.

In the present embodiment, the lower portion 31B is formed in a column whose diameter is larger than the diameter of the upper portion 31A. However, the lower portion of the deformable portion according to the present invention may also be formed in a column whose diameter is smaller than the diameter of the upper portion, or a column whose diameter is equal to the diameter of the upper portion.

The upper portion 31A of the deformable portion 31 is inserted into the tube hole 27a of the connector fitting portion 27 of the housing 2. The outer diameter of the upper portion 31A is larger than the diameter of the tube hole 27a of the connector fitting portion 27. Therefore, when the upper portion 31A of the deformable portion 31 is inserted into the tube hole 27a of the connector fitting portion 27, the upper portion 31A is compressed by the connector fitting portion 27 (the male connector connecting portion 6). Further, the top surface 31a is a flat surface perpendicular to the axial direction of the deformable portion 31, and is exposed from the connector fitting portion 27 (the male connector connecting portion 6).

The lower portion 31B of the deformable portion 31 is inserted into the tube hole of the inner tubular portion 24 of the housing 2. The outer diameter of the lower portion 31B of the deformable portion 31 is larger than the inner diameter of the inner tubular portion 24. Therefore, when the lower portion 31B of the deformable portion 31 is inserted into the tube hole of the inner tubular portion 24, the lower portion 31B is compressed by the inner tubular portion 24.

A recess 34, which is curved to be recessed toward the top surface 31a, is formed on the bottom surface 31b of the deformable portion 31 (see FIG. 4). By providing the recess 34, the thickness of the valve 3 can be reduced. As a result, it is possible to easily deform the valve 3 when connecting the male connector 100 thereto.

Figure 6:
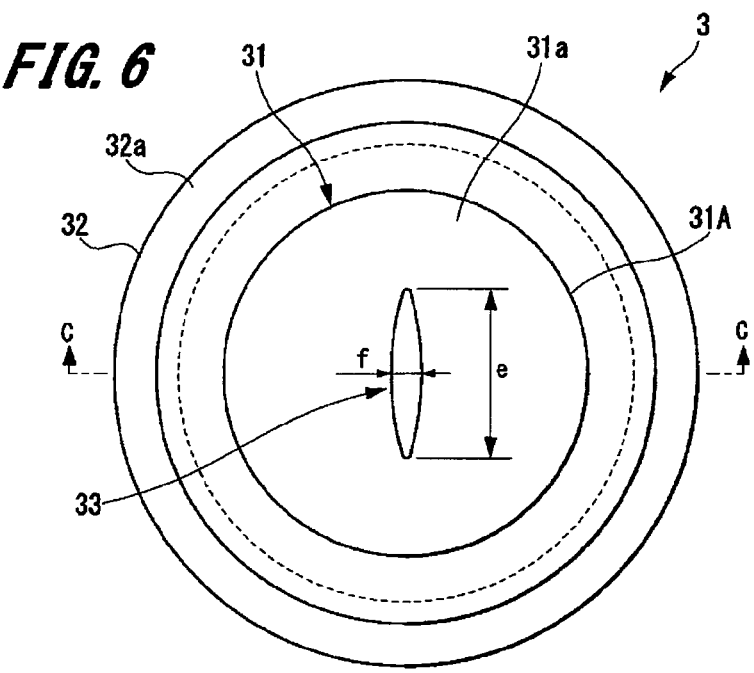
FIG. 6 is a plan view of the valve of the connector according to the first embodiment of the present invention.

As illustrated in FIGS. 5 and 6, the slit 33 is opened on the top surface 31a of the deformable portion 31. The slit 33 is formed in a linear shape extending in the radial direction of the deformable portion 31, and has a predetermined width. The slit 33 is formed by a projection for slit formed in the mold (not illustrated).

When the valve 3 is attached to the male connector connecting portion 6, the upper portion 31A and the lower portion 31B of the deformable portion 31 are compressed by the male connector connecting portion 6. Accordingly, the slit 33 is closed, with the valve 3 attached to the male connector connecting portion 6. Therefore, the male connector connecting portion 6 is blocked by the valve 3 (see FIG. 3).

As illustrated in FIG. 6, both ends in the longitudinal direction of the slit 33 are each formed in an arc shape. Accordingly, when the valve 3 is pressed by the male connector 100 (see FIG. 5) and thereby elastically deforms, both ends of the slit 33 are less likely to be torn. As a result, it is possible to improve the durability of the valve 3.

For example, when forming a slit in a valve using a blade, both ends of the slit cannot be formed in an arc shape. Therefore, when the valve is pressed by a male connector and thereby elastically deforms, stress is concentrated on two points, namely, the both ends of the slits. As a result, both ends of the slit are likely to be torn.

The length e in the longitudinal direction of the slit 33 is preferably within the range of 1 to 4 mm. If the length e of the slit 33 is too short, the openability of the valve 3 while elastically deforming will become worse. On the other hand, if the length e of the slit 33 is too long, the male connector 100 (see FIG. 8) will disadvantageously enter the slit 33.

Further, the width f which is the length in the short-length direction of the slit 33 is preferably within the range of 0.1 to 0.6 mm when taking into consideration that the slit 33 is closed when the valve 3 is compressed by the male connector connecting portion 6.

Figure 7:
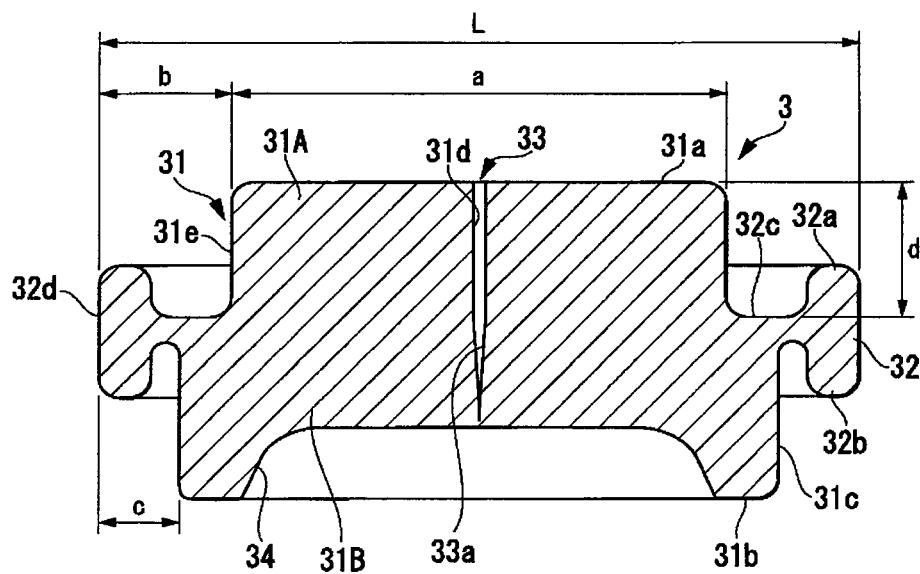
FIG. 7 is a cross-sectional view taken along line C-C of FIG. 6.

As illustrated in FIG. 7, the slit 33 has a tapered portion 33a whose opening becomes narrower toward the end thereof. Further, an end of the slit 33, the end being located on the opposite side of the top surface 31a, does not reach the recess 34 and is located within the deformable portion 31. In other words, a slight distance (0.01 to 1.0 mm, for example) is ensured between the end of the slit 33 located on the opposite side of the top surface 31a and the recess 34, and the slit 33 therefore does not communicate with the flow path 13 (see FIG. 4) of the housing 2.

When pressing force is applied onto the top surface 31a of the deformable portion 31 by the male connector 100, the deformable portion 31 elastically deforms. Accordingly, an inner surface 31d (see FIG. 7) of the deformable portion 31, the inner surface 31d forming the slit 33, deforms to rotate in the clockwise direction and the counterclockwise direction from the axis (i.e., radially with respect to the axis), so as to face the flow path 13 of the housing 2.

At this time, a part of the deformable portion 31, the part being located between the tip end of the slit 33 and the recess 34, is torn, so that the slit 33 communicates with the flow path 13. As with the inner surface of the deformable portion 31, the top surface 31a of the valve 3 deforms to rotate with respect to the axis of the deformable portion 31, so as to form an opening 38 (see FIG. 8) which communicates with the flow path 13.

The fixing portion 32 is continuous with the outer peripheral surface 31c of the lower portion 31B of the deformable portion 31, and protrudes outward in the radial direction of the deformable portion 31. The fixing portion 32 has an upper fixing piece 32a and a lower fixing piece 32b each of which protrudes in the axial direction of the deformable portion 31, and a flat surface 32c which is continuous with the outer peripheral surface of the deformable portion 31. The upper fixing piece 32a and the lower fixing piece 32b are each formed in a ring-like shape that is concentric with the deformable portion 31. The upper fixing piece 32a is fitted into the recess 27c of the connector fitting portion 27, and the lower fixing piece 32b is fitted into the fitting recess 24a of the inner tubular portion 24 of the housing 2 (see FIG. 4).

Next, the dimensions of the valve 3 will be described with reference to FIG. 7.

The diameter a of the upper portion 31A of the deformable portion 31 is preferably within the range of 3 to 5 mm. If the diameter a is smaller than 3 mm, the diameter a will be smaller than the inner diameter of the male connector 100 (see FIG. 8) and the upper portion 31A of the deformable portion 31 may enter the male connector 100. If the upper portion 31A of the deformable portion 31 enters the male connector 100, the valve 3 will not elastically deform to open the slit 33.

Here, the distance between an outer peripheral surface 31e of the upper portion 31A of the deformable portion 31 and an outer peripheral surface 32d of the fixing portion 32 is defined as "distance b", and the distance between the outer peripheral surface 31c of the lower portion 31B of the deformable portion 31 and the outer peripheral surface 32d of the fixing portion 32 is defined as "distance c". Further, the distance between the top surface 31a of the deformable portion 31 and the flat surface 32c of the fixing portion 32 is defined as "distance d". In order to reliably fix the valve 3 to the housing 2, the distances c and d are equal to or larger than 0.5 mm. Further, the distance b is preferably within the range of 0.5 to 2.0 mm. For example, when both of the distance b and the distance c are 0.5 mm, the diameter of the upper portion 31A and the diameter of the lower portion 31B in the deformable portion 31 are equal to each other.

The outer diameter L of the fixing portion 32 is preferably within the range of 5 to 7 mm. If the outer diameter L is too large, the outer diameter of the housing 2 also has to be set large. In this case, the screw portion 27d of the connector fitting portion 27 may not have a size that corresponds to the lock portion (the lure lock) of a male connector. On the other hand, if the outer diameter L is too small, the openability of the valve 3 while elastically deforming will become worse. Further, since the deformation amount of the valve 3 in the axial direction has to be made larger, the fixing property of the valve 3 with respect to the housing 2 will become worse.

In the present embodiment, the diameter A of the upper portion 31A of the deformable portion 31 is set to approximately 4.1 mm, and the diameter of the lower portion 31B of the deformable portion 31 is set to approximately 5.1 mm. Further, the length in the axial direction of the deformable portion 31 is set to 3 mm, and the depth of the recess 34 on the bottom surface 31b is set to approximately 0.7 mm. As a result, the length in the axial direction of the central part of the deformable portion 31 is approximately 2.3 mm.

In order to allow the valve 3 to elastically deform so that the top surface 31a forms the opening 38 (see FIG. 8) which communicates with the flow path 13, the thickness of the central part of the deformable portion 31 is preferably equal to or less than 4.0 mm.

Further, the outer diameter L of the fixing portion 32 is set to approximately 6.2 mm, and the thickness of the fixing portion 32 is set to approximately 0.7 mm.

The compressibility of the fixing portion 32 is preferably equal to or higher than 50%.

[Connection between Connector and Male Connector]

Next, the connection between the connector 1 and the male connector 100 will be described with reference to FIG. 8.

Figure 8:
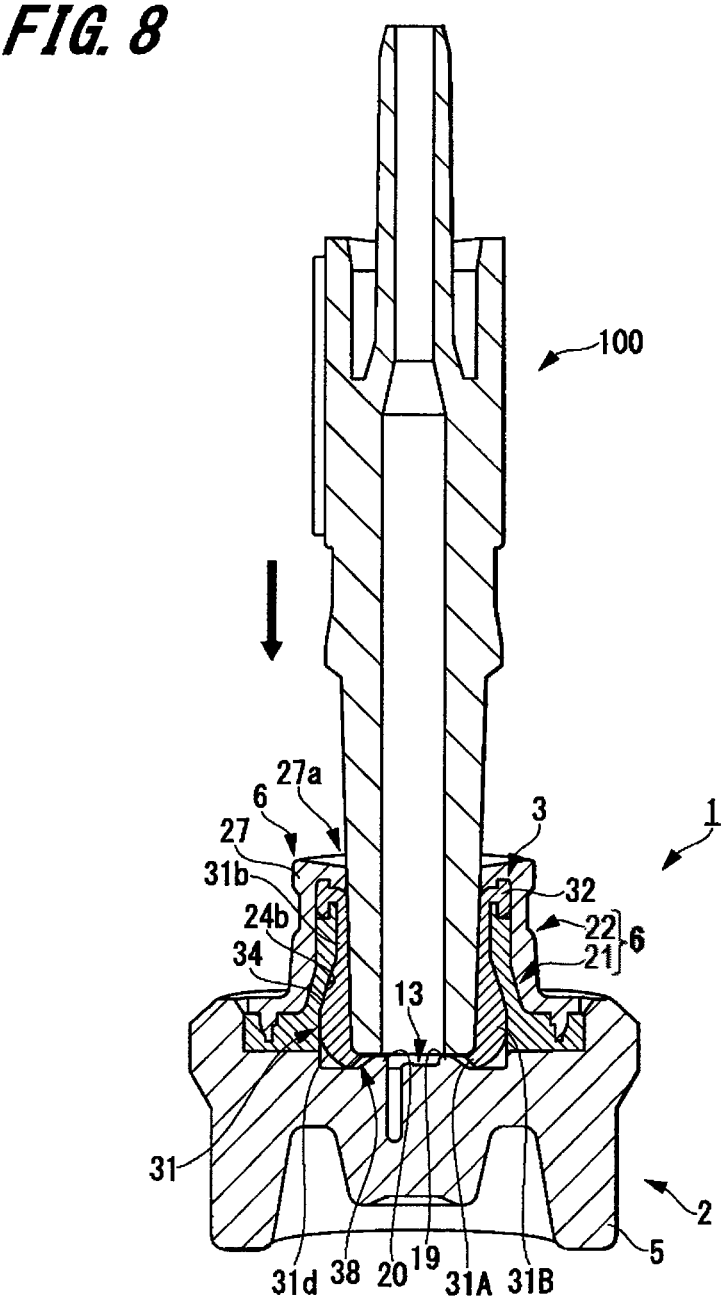
FIG. 8 is a cross-sectional view taken along line B-B of FIG. 1 illustrating a state in which a male connector is connected to the connector according to the first embodiment of the present invention.

FIG. 8 is a cross-sectional view illustrating a state in which the male connector 100 is connected to the connector 1.

The male connector 100 is a portion or an instrument connected to the male connector connecting portion 6 of the connector 1. Examples of the male connector 100 include a part of a syringe (an injection device) to be connected by a needle tube, and a tubular instrument (such as a lure taper member and a sheath).

In order to connect the male connector 100 to the connector 1, first, the tip end of the male connector 100 is caused to face the male connector connecting portion 6 of the connector 1. Since the diameter of the male connector 100 continuously decreases toward the tip end thereof, the male connector 100 is liquid-tightly fitted to the connector fitting portion 27 of the male connector connecting portion 6.

Next, the tip end of the male connector 100 is inserted into the tube hole 27a of the connector fitting portion 27 to thereby press the top surface 31a of the deformable portion 31 of the valve 3 by the tip end of the male connector 100. By pressing the top surface 31a of the valve 3 by the tip end of the male connector 100, the deformable portion 31 of the valve 3 elastically deforms downward. Accordingly, the upper portion 31A is displaced so as to sink into the lower portion 31B. Further, the lower portion 31B is displaced toward the flow path 13 while elastically deforming.

At this time, the top surface 31a of the valve 3 abuts the tip end of the male connector 100. Further, the upper portion 31A of the deformable portion 31 sinks into the lower portion 31B, and the lower portion 31B is thereby displaced toward the flow path 13. As a result, the part of the slit 33 between the tip end of the slit 33 and the recess 34 (see FIG. 7) is torn, so that the slit 33 communicates with the flow path 13. In other words, the slit 33 extends in the depth direction thereof to penetrate the deformable portion 31.

In such a state, the tip end of the male connector 100 is further inserted into the tube hole 27a of the connector fitting portion 27. Accordingly, as illustrated in FIG. 8, the tip end face of the male connector 100 comes to abut the stopping portions 19, 20, and the insertion length of the male connector 100 with respect to the connector 1 is thereby defined. At this time, the peripheral surface of a part of the male connector 100 from the tip end toward the base end is liquid-tightly fitted to the connector fitting portion 27.

As a result, it is possible to prevent the male connector 100 from penetrating the valve 3. Thus, it is possible to reliably prevent the male connector 100 from entering the flow path 13. Further, since the deformable portion 31 is prevented from being forcibly caused to deform due to unnecessary external force applied to the valve 3, it is possible to suppress or prevent the slit 33 of the valve 3 from being torn. Therefore, the air-tightness of the valve 3 can be maintained.

In the male connector 100 illustrated in FIG. 8, a lock portion (lure lock) is not provided. Therefore, the male connector 100 may penetrate the valve 3 if the stopping portion 19, 20 are not provided. Therefore, it is extremely effective to provide the stopping portions 19, 20.

Further, since the stopping portions 19, 20 are each formed in a projection shape protruding upward, even when the male connector 100 abuts the stopping portions 19, 20, the flow path 13 is formed between the male connector 100 and the connecting wall 18. Therefore, even when the male connector 100 is in connection with the connector 1, liquid such as a medical solution flowing from the first tube connecting port 11 can flow over the connecting wall 18, and flow into the second tube connecting port 12.

Further, even when a male connector that has a lock portion (lure lock) is used, if there is a certain variation in the dimension of the lock portion depending on manufactures, it is not possible to accurately define the insertion length of the male connector with respect to the connector 1. Therefore, the provision of the stopping portions 19, 20 is effective also when using a male connector having a lock portion (lure lock).

By inserting the male connector 100 until the tip end face of the male connector 100 abuts the stopping portions 19, 20, the deformable portion 31 of the valve 3 deforms by being pressed by the male connector 100 and thereby arranged around the stopping portions 19, 20. Specifically, the surface of the recess 34 of the deformable portion 31 of the valve 3 is pressingly expanded toward the tapered surface 24b of the inner tubular portion 24 of the housing 2.

Further, the inner surface 31d of the valve 3 deforms to radially rotate with respect to the axis so as to face the flow path 13 of the housing 2, while the bottom surface 31b warps toward the lateral side of the valve 3. Further, the top surface 31a of the valve 3 is displaced so as to form a peripheral surface that surrounds the axis, so that the opening 38 which communicates with the flow path 13 of the housing 2 is formed. As a result, the connection of the male connector 100 to the connector 1 is completed.

In the state where the connection of the male connector 100 to the connector 1 has been completed, the tip end face and a part of the outer peripheral surface of the male connector 100 are in liquid-tight contact with the elastically deformed deformable portion 31. Therefore, the liquid-tightness between the connector 1 and the male connector 100 can be reliably ensured.

Further, since a part of the top surface 31a of the valve 3 forms the opening 38 and the other part thereof has contact with the tip end of the male connector 100, the tip end of the male connector 100 does not enter the flow path 13. Therefore, it is possible to prevent the tip end of the male connector 100 from making contact the liquid in the flow path 13, and therefore reduce the risk of the liquid in the flow path 13 being contaminated.

Further, the path extending from the tip end of the male connector 100 to the flow path 13 of the housing 2 is equal to the length in the axial direction of the opening 38 formed by the top surface 31a. Thus, the path extending from the tip end of the male connector 100 to the flow path 13 can be made shorter, thereby making it possible to prevent or suppress the liquid from being accumulated in the valve 3.

In other words, the connector 1 makes it possible not only to prevent the male connector 100 from entering the flow path 13, but also to prevent or suppress the liquid from being accumulated in the valve 3.

Further, in the connector 1, the tapered surface 24b is formed on the inner surface of the inner tubular portion 24 of the male connector connecting portion 6. Thus, when the top surface 31a of the valve 3 is pressed, the deformation of the lower portion 31B of the valve 3 can be guided by the tapered surface 24b. As a result, not only the bottom surface 31b can be reliably caused to warp toward the lateral side of the valve 3, but also the inner surface 31d can be reliably caused to face the flow path 13 of the housing 2.

Further, in the connector 1, the stopping portions 19, 20 are each formed in a projection shape protruding in the direction opposite to the insertion direction of the male connector 100. Further, a space in which the deformed valve 3 is arranged is ensured around the stopping portions 19, 20. Accordingly, the insertion length of the male connector 100 can be defined by the stopping portions 19, 20 without disturbing the deformation of the valve 3.

Further, in the connector 1, the stopping portions 19, 20 are each formed in a tapered shape whose diameter decreases toward the end thereof. Accordingly, the strength of the stopping portions 19, 20 can be ensured without disturbing the deformation of the valve 3. Further, it is possible to minimize the contact area between the tip end of the male connector 100 and the stopping portions 19, 20. As a result, the risk of contamination of the stopping portions 19, 20 can be reduced.

Further, in the connector 1, the stopping portions 19, 20 can be arranged at positions facing the respective ends in the longitudinal direction of the slit 33. Accordingly, it is possible to minimize the area in which the tip end of the male connector 100 is exposed to the flow path 13 of the housing 2. As a result, the risk of the contamination of the liquid in the flow path 13 can be further reduced. Further, it is possible to minimize the deformation of the valve 3, and thereby suppress or prevent the slit 33 from being torn.

To remove the male connector 100 from the connector 1, the male connector 100 is pulled from the connector fitting portion 27. Accordingly, the valve 3 is released from the pressure of the tip end of the male connector 100, and restored to the state of blocking the male connector connecting portion 6 (see FIG. 3).

In the present embodiment, the tip end of the slit 33 of the valve 3 after being molded does not reach the recess 34 and is located within the deformable portion 31. Further, the valve 3 with the slit 33 not penetrating the deformable portion 31 is fixed to the male connector connecting portion 6 of the housing 2.

However, as the valve 3 according to the present invention, a cut may be made in the recess 34 so that the slit 33 penetrates the deformable portion 31 before fixing the valve 3 to the male connector connecting portion 6. Also in this case, the slit 33 is compressed and thereby closed in a state where the valve 3 is attached to the male connector connecting portion 6. Therefore, the male connector connecting portion 6 is blocked by the valve 3.

2. Second Embodiment of Connector

Next, a connector according to the second embodiment of the present invention will be described with reference to FIG. 9.

Figure 9:
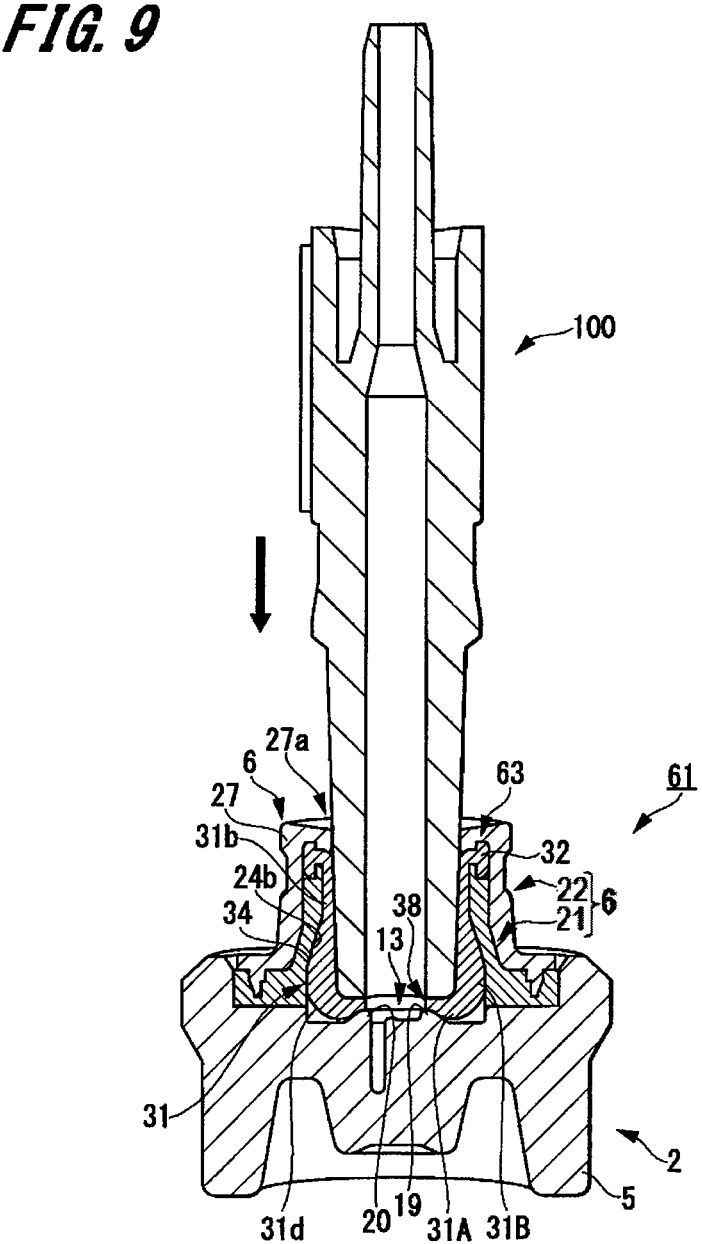
FIG. 9 is a cross-sectional view illustrating a state in which a male connector is connected to a connector according to a second embodiment of the present invention.

FIG. 9 is a cross-sectional view illustrating a state in which a male connector 100 is connected to the connector according to the second embodiment of the present invention.

The connector of the second embodiment has the same configuration as that of the connector 1 of the first embodiment. The connector of the second embodiment differs from the connector 1 of the first embodiment only in a state of a valve 63 when the male connector 100 is connected thereto. Thus, herein the description will focus on the valve 63, and the same components as those of the connector 1 will be denoted by the same reference numerals and description thereof will be omitted.

As illustrated in FIG. 9, the valve 63 of a connector 61 has the same configuration as that of the valve 3 of the first embodiment. The valve 63 differs from the valve 3 only in the deformation of a deformable portion 31. When the tip end of the male connector 100 is inserted into a tube hole 27a of a connector fitting portion 27, the tip end of the male connector 100 abuts stopping portions 19, 20 through the deformable portion 31 of the valve 63. As a result, the insertion length of the male connector 100 with respect to the connector 1 is defined. That is, the deformable portion 31 of the valve 63 is interposed between the stopping portions 19, 20 and the tip end of the male connector 100.

At this time, the peripheral surface of a part of the male connector 100 from the tip end toward the base end is liquid-tightly fitted to the connector fitting portion 27.

Also in this case, as with the first embodiment, it is possible to prevent the male connector 100 from penetrating the valve 63, and thereby reliably prevent the male connector 100 from entering the flow path 13. Further, it is possible to suppress or prevent the slit 33 of the valve 63 from being torn, and thereby maintain the air-tightness of the valve 63.

Since the deformation of the deformable portion 31 of the valve 63 is the same as the deformation of the deformable portion 31 of the valve 3, description thereof will be omitted. Further, also in the connector 61, the same effect as that in the first embodiment can be obtained. More specifically, the connector 61 makes it possible not only to prevent the male connector 100 from entering the flow path 13, but also to prevent or suppress the liquid from being accumulated in the valve 63.

Hereinabove, embodiments of the connector according to the present invention have been described including the effects thereof. However, the connector of the present invention is not limited to the embodiments described above, and various modifications can be made without departing from the scope of the invention described in the claims.

In the above embodiments, the linear slit 33 is formed in the valves 3, 63. However, as the valve according to the present invention, a cross-shaped slit may be formed, for example. When forming a cross-shaped slit, the angle at which two straight lines intersect can be set to any angle.

Further, as the valve according to the present invention, for example, a slit that is opened on the top surface 31a of the deformable portion 31 may be formed in a linear shape and a slit that is opened on the recess 34 may be formed in a cross shape. In this case, the linear slit can maintain the air-tightness, and the cross-shaped slit can allow the valve 3 to easily deform.

What is claimed is:

1. A connector comprising:
   a housing comprising:
     a flow path configured to allow liquid to pass therethrough, and
     a male connector connecting portion to which a male connector is connectable, the male connector connection portion comprising a substantially circular tube hole communicating with the flow path; and
   a valve formed as a separate member from the housing, the valve being formed of an elastic material and adapted to block the male connector connecting portion of the housing, wherein the valve includes:
     a top surface exposed from the male connector connecting portion,
     a bottom surface opposite to the top surface, and
     a slit opened at least on the top surface or the bottom surface,
   wherein the housing includes at least one projection that protrudes upward and is configured to define an insertion length of the male connector,
   wherein each of the at least one projection comprises:
     an outer surface portion that faces away from a central axis of the male connector connecting portion, and
     an inner surface portion that faces toward the central axis of the male connector connecting portion,
   wherein the connector is configured such that:
     when the male connector is not disposed in the connector, the valve does not contact the at least one projection, and
     when the male connector is disposed in the connector, the male connector causes the valve to contact at least the outer surface portion of the at least one projection, and
   wherein the at least one projection is located such that, when the liquid passes through the flow path of the housing, the liquid contacts at least the inner surface portion of the at least one projection.

2. The connector according to claim 1, wherein the valve is configured such that, when the male connector is disposed in the connector, a portion of the valve is interposed between the at least one projection and the tip end of the male connector.

3. The connector according to claim 1, wherein the valve is configured such that, when the male connector is disposed in the connector, a portion of the valve is arranged outward of the outer surface portion of the at least one projection.

4. The connector according to claim 1, wherein the at least one projection is formed in a tapered shape with a diameter that decreases toward a top end thereof.

5. The connector according to claim 1, wherein
   the slit of the valve is linear, and
   the at least one projection is arranged at a position facing a longitudinal end of the slit.

6. The connector according to claim 1, wherein the valve includes:
   a deformable portion that is displaced toward the flow path while elastically deforming when the male connector is disposed in the connector, so that an inner surface forming the slit faces the flow path of the housing and the top surface forms an opening communicating with the flow path, and
   a fixing portion that protrudes at an intermediate position between the top surface and the bottom surface from an outer peripheral surface of the deformable portion and is fixed to the housing.

7. The connector according to claim 1, wherein the housing includes:
   a housing main body,
   a first member joined to the housing main body and forming a base end of the male connector connecting portion, and
   a second member joined to the first member and forming a tip end of the male connector connecting portion.

8. The connector according to claim 7, wherein:
   the valve includes:
     a deformable portion that is displaced toward the flow path while elastically deforming when the male connector is disposed in the connector, so that an inner surface forming the slit faces the flow path of the housing and the top surface forms an opening communicating with the flow path, and
     a fixing portion that protrudes at an intermediate position between the top surface and the bottom surface from an outer peripheral surface of the deformable portion and is fixed to the housing, and
   the fixing portion is fixed in a fitting recess formed between a portion of the first member and a portion of the second member.

9. The connector according to claim 7, wherein:
   the first member includes:
     an inner tubular portion, and
     a flange portion protruding radially from the inner tubular portion, and
   the flange portion is fitted to a step portion of the housing main body.

10. The connector according to claim 7, wherein:
    the second member includes a connector fitting portion configured to receive the male connector, and
    the connector fitting portion includes a tapered surface on an inner surface of the connector fitting portion.

11. The connector according to claim 10, wherein:
    the second member includes an outer tubular portion having an inner diameter that is larger than an inner diameter of the connector fitting portion.

12. The connector according to claim 10, wherein:
    the second member includes an outer tubular portion, and
    the connector fitting portion includes a screw portion on outer peripheral surfaces of the connector fitting portion and the outer tubular portion.

13. The connector according to claim 7, wherein:
    the second member includes an outer tubular portion,
    the outer tubular portion includes an engagement portion protruding radially outward from the outer tubular portion, and
    the engagement portion includes an engagement projection extending from a lower surface of the engagement portion and engaging with an engagement groove formed in the first member.

14. The connector according to claim 1, wherein the valve includes:
    an upper portion and a lower portion, the lower portion having an outer diameter that is larger than an upper diameter of the upper portion.

15. The connector according to claim 1, wherein the valve includes a recess formed in the bottom surface of the valve.

16. The connector according to claim 1, wherein the slit of the valve is linear, and both ends of the linear slit are formed in an arc shape.

17. The connector according to claim 1, wherein the slit does not extend entirely through the valve in an axial direction of the valve, and a portion of the valve formed between an axial end of the slit and the flow path is configured to tear upon insertion of the male connector into the connector.

18. A method comprising:
providing a male connector;
providing a connector comprising:
  a housing comprising:
    a flow path configured to allow liquid to pass therethrough, and
    a male connector connecting portion to which a male connector is connectable, the male connector connection portion comprising a substantially circular tube hole communicating with the flow path; and
  a valve formed as a separate member from the housing, the valve being formed of an elastic material and adapted to block the male connector connecting portion of the housing, wherein the valve includes:
    a top surface exposed from the male connector connecting portion;
    a bottom surface opposite to the top surface; and
    a slit opened at least on the top surface or the bottom surface,
  wherein the housing includes at least one projection that protrudes upward and is configured to define an insertion length of the male connector,
  wherein each of the at least one projection comprises:
    an outer surface portion that faces away from a central axis of the male connector connecting portion, and
    an inner surface portion that faces toward the central axis of the male connector connecting portion,
  inserting the male connector into the connector such that the tip end of the male connector is prevented by the stopping portion from entering the flow path,
  wherein:
    when the male connector is not disposed in the connector, the valve does not contact the at least one projection, and
    when the male connector is disposed in the connector, the male connector causes the valve to contact at least the outer surface portion of the at least one projection, and
  wherein the at least one projection is located such that, when the liquid passes through the flow path of the housing, the liquid contacts at least the inner surface portion of the at least one projection.

19. The method of claim 18, wherein, when the male connector is disposed in the connector, a portion of the valve is interposed between the at least one projection and the tip end of the male connector.

* * * * *